Figure 1:
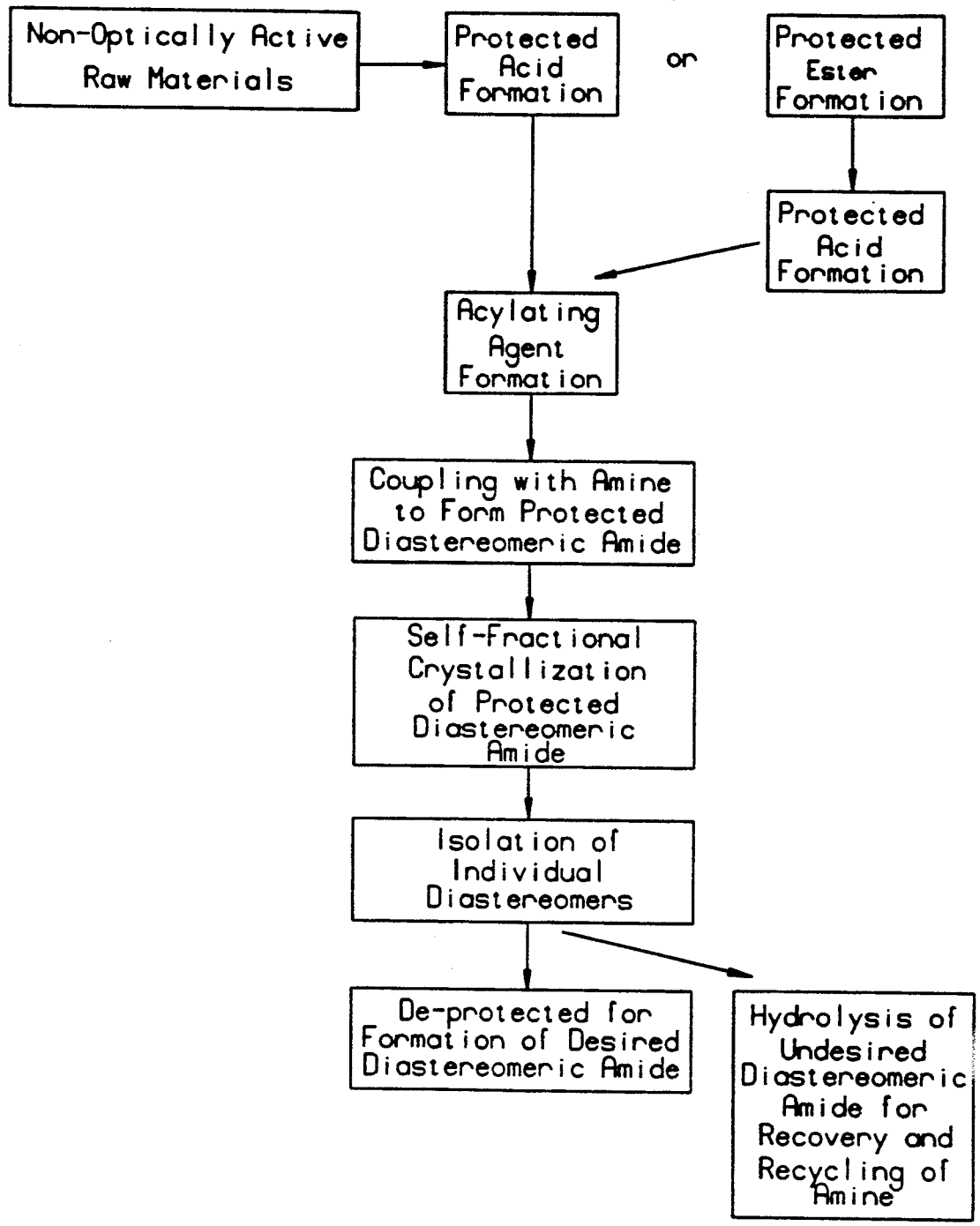

United States Patent [19]

Zepp

[11] Patent Number: 5,237,073
[45] Date of Patent: Aug. 17, 1993

[54] DERIVATIVES AND PRECURSORS OF CAPTOPRIL AND ITS ANALOGUES

[75] Inventor: Charles M. Zepp, Berlin, Mass.

[73] Assignee: Sepracor, Inc., Marlborough, Mass.

[21] Appl. No.: 664,515

[22] Filed: Mar. 5, 1991

Related U.S. Application Data

[63] Continuation of Ser. No. 237,605, Aug. 26, 1988, abandoned.

[51] Int. Cl.⁵ .......................................... C07D 403/12
[52] U.S. Cl. .................................... 548/523; 548/519
[58] Field of Search .................. 548/523; 514/422

[56] References Cited

U.S. PATENT DOCUMENTS

| | | | |
|---|---|---|---|
| 4,105,776 | 8/1978 | Ondetti et al. | 424/274 |
| 4,288,368 | 9/1981 | Haugwitz | 548/523 X |
| 4,297,282 | 10/1981 | Ohashi et al. | 260/326.2 |
| 4,372,960 | 2/1983 | L'Italien | 548/523 X |
| 4,788,212 | 11/1988 | Scolastico | 548/523 X |

FOREIGN PATENT DOCUMENTS

| | | |
|---|---|---|
| 0035336 | 9/1981 | European Pat. Off. . |
| 2066243A | 7/1981 | United Kingdom . |
| 2170806A | 8/1986 | United Kingdom . |

OTHER PUBLICATIONS

Chemical Abstracts, vol. 109, Abstract No. 50146S (1988), Dan et al.
Chemical Abstracts, vol. 106, Abstract No. 58866k (1987), Schroeter, et al.
Chemical Abstracts, vol. 97, Abstract No. 5495c (1988), Dynamic.
Chemical Abstracts, vol. 87, Abstract No. 52725f (1977), Mustafaev, et al.
Wilen et al., *Tetrahedron*, vol. 33: pp. 2725–2736 (1977).

*Primary Examiner*—Joseph Paul Brust
*Attorney, Agent, or Firm*—Pennie & Edmonds

[57] ABSTRACT

This invention relates to novel S-protected derivatives of an orally active inhibitor of an angiotensin-converting enzyme (ACE) and its analogues, which derivatives are useful for the reasons that they are (1) easily prepared from novel precursors, (2) resolvable to their optically purified stereoisomeric species and (3) convertible to non-derivatized stereoisomeric species which correspond to the pharmacologically active inhibitor and its analogues. Consequently, this invention also relates to the novel precursors. Novel methods for preparing the derivatives and their precursors are also noted herein. In addition, methods for converting the derivatives to the resolved de-derivatized stereoisomeric species of the ACE inhibitor and its analogues are described.

13 Claims, 1 Drawing Sheet

5,237,073

DERIVATIVES AND PRECURSORS OF CAPTOPRIL AND ITS ANALOGUES

CROSS REFERENCE TO RELATED APPLICATIONS

The present application, Ser. No. 07/664,515, filed Mar. 5, 1991 is a continuation of U.S. patent application, Ser. No. 07/237,605 filed Aug. 26, 1988, now abandoned.

TABLE OF CONTENTS 1.0 Introduction
2.0 Background of the Invention
  2.1 Significance of Optical Purity
  2.2 Conventional Means of Obtaining Optically Pure Compounds
  2.3 Stereospecific Resolutions of Enzyme-Catalyzed Bioconversions of Organic Compounds
3.0 Summary of the Invention
4.0 Brief Description of the Figures
5.0 Detailed Description of the Invention
  5.1 Novel Compositions of Matter Pertaining To Derivatives and Precursors of Captopril And Its Analogues
    5.1.1 Thiol-protected Derivatives of Captopril and its Analogues
    5.1.2 Precursors of the Thiol-protected Derivatives Of Captopril and its Analogues
  5.2 Method for Preparing Captopril and its Analogues, and Their Thiol-protected Derivatives and Precursors
    5.2.1 Preparations of Thio-Protected Derivatives of Captopril and its Analogues
    5.2.2 Preparations of Precursors of Thio-Protected Derivatives of Captopril and its Analogues
    5.2.3 Preparations of Captopril and its Analogues From Their Thio-Protected Derivatives
6.0 Examples
  6.1 Preparation of 2-Methyl-3-(S-pyrrolidinothioxomethylthiopropanoic Acid (XXXII)
  6.2 Preparation of N-[2-Methyl-3-(S-pyrrolidinothioxomethyl)thiopropanoyl] L-Proline (XXXIII) Using Two Reaction Solvents
  6.3 Preparation of N-[2-Methyl-3-(S-pyrrolidinothioxomethyl)thiopropanoyl] L-Proline (XXXIII) Using a Single Reaction Solvent
  6.4 Preparation of Methyl Ester of N-[2-methyl-3-(S-pyrrolidinothioxomethyl) thiopropanoyl] L-Proline (XXXIV) Using Esterified Reactant
  6.5 Preparation of Methyl Ester of N-[2-methyl-3-(S-pyrrolidinothioxomethyl) thiopropanoyl] L-Proline (XXXIV) By Esterification Step
  6.6 Preparation of t-Butyl Ester of N-[2-Methyl-3-(S-pyrrolidinothioxomethyl)thiopropanoyl] L-Proline (XXXV)
  6.7 Preparation of Methyl Ester of N-[2-Methyl-3-(S-pyrrolidinocarbonyl) thiopropanoyl] L-Proline (XXXVI)
  6.8 Preparation of N-[2-Methyl-3-(thiopropanoyl] L-Proline (Captopril) (XXXVII)

1.0 INTRODUCTION

This invention relates to novel S-protected derivatives of an orally active inhibitor of an angiotensin-converting enzyme (ACE) and its analogues, which derivatives are useful for the reasons that they are (1) easily prepared from novel precursors, (2) resolvable to their optically purified stereoisomeric species and (3) convertible to non-derivatized stereoisomeric species which correspond to the pharmacologically active inhibitor and its analogues. Consequently, this invention also relates to the novel precursors.

Novel methods for preparing the derivatives and their precursors are also noted herein. In addition, methods for converting the derivatives to the resolved de-derivatized stereoisomeric species of the ACE inhibitor and its analogues are described.

2.0 BACKGROUND OF THE INVENTION

Enzymatic resolution and fractional crystallization procedures have long been known and exploited for resolving racemic mixtures. Unfortunately, many chiral compounds of commercial significance are not adequately prepared using these procedures.

2.1 Significance of Optical Purity

Many organic compounds exist in optically active forms, i.e., they have the ability to rotate the plane of plane-polarized light. The property of optical activity is due to molecular asymmetry about carbon atoms that are linked to four different atoms or chemical groups. In describing an optically active compound, the prefixes D and L or R and S are used to denote the configuration of the molecule about its chiral center(s). The prefixes (+) and (−) or d and l are employed to designate the sign of rotation of plane-polarized light by the compound, with (−) or l meaning that the compound is levorotatory. A compound prefixed with (+) or d is dextrorotatory. Compounds of a given chemical structure, which differ from one another only in the configuration of chemical groups about one asymmetric carbon atom, or chiral center as it is sometimes called, are called stereoisomers. Where there are n asymmetric carbons or chiral centers, the number of potential stereoisomers increases to $2^n$. Thus, a molecule with three chiral centers would have eight possible stereoisomers.

Where these stereoisomers are identical except that they are non-superimposable mirror images of one another, the molecules are referred to as enantiomers. Stereoisomers which are not non-superimposable mirror images of other stereoisomers of the same compound are described as diastereomers (e.g. 2R,3R-tartaric acid and 2R,3S-tartaric acid are diastereomers whereas 2R,3R-tartaric acid and 2S,3S-tartaric acid are enantiomers). A mixture of enantiomers is called an enantiomeric or racemic mixture, and as used herein this term is applied to mixtures of enantiomers in any proportion. A mixture of diastereomers is referred to as a diastereomeric mixture, where as the term is used herein the diastereomers may be present in any proportion.

While the structural differences between stereoisomers are subtle and of little consequence in ordinary chemical reactions, they may be profound where biological systems are concerned, i.e., if the compounds are utilized in enzyme-catalyzed reactions. Thus, the L-amino acids are metabolized in humans but the corresponding D-analogs are not, and only D-glucose can be phosphorylated and processed into glycogen or degraded by the glycolytic and oxidative pathways of intermediary metabolism. Similarly, beta blockers, pheromones, prostaglandins, steroids, flavoring and fragrance agents, pharmaceuticals, pesticides, herbicides and many other compounds exhibit critical stereospecificity. In the field of pesticides, Tessier [Chemistry and Industry, Mar. 19, 1984, p. 199] has shown that only two of the eight stereoisomers of deltamethrin, a pyrethroid insecticide, have any biological activity. The same statement concerning the concentration of bioactivity in a single isomer can be made about many other pesticides, including the phenoxypropanoates and halopropanoate derivatives, each containing one chiral center and existing in the form of two optical isomers.

Stereochemical purity is of equal importance in the field of pharmaceuticals, where 12 of the 20 most prescribed drugs exhibit chirality. A case in point is provided by naproxen, or (+)-S-2-(6-methoxy-2-naphthyl)-propanoic acid, which is one of the two most important members of a class of 2-arylpropanoic acids with non-steroidal anti-inflammatory activity used, for instance, in the management of arthritis. In this case, the S(+) enantiomer of the drug is known to be 28 times more therapeutically potent than its R(−) counterpart. Still another example of chiral pharmaceuticals is provided by the family of beta-blockers; the L-form of propranolol is known to be 100 times more potent than the D-enantiomer.

In particular, interest in captopril exists since it belongs to a new class of antihypertensive agents. Its specific action resides in its acting as a specific competitive inhibitor of angiotensin I-converting enzyme (ACE) which converts angiotensin I to angiotensin II. Although the actual mechanism of its action is not fully elucidated, it has been shown that captopril reduces blood pressure and results in beneficial hemodynamic effects in patients with congestive heart failure. More specifically, captopril (commercially available from Squibb as CAPOTEN TM), contains a 2-methyl-3-thiolpropanoyl segment linked via an amide bond to L-proline. When the chiral carbon atom in the 2-methyl-3-thiopropanoyl segment has the S-configuration, this diastereomer is known to be 100 times more active than the corresponding diastereomer where the segment has the R-configuration. Consequently, a variety of methods to produce captopril have been undertaken, including preparation by enzymatic resolution and by fractional crystallization of its diastereomers.

Synthesis of compounds with asymmetric centers by standard organic synthetic techniques generally leads to a racemic or diastereomeric mixture which, in the aggregate, may have a relatively low specific bioactivity since certain of the stereoisomers in the mixture are likely to be biologically inactive. As a result, larger quantities of the material must be used to obtain an effective dose, and manufacturing costs are increased due to the co-production of stereochemically "incorrect" and hence, inactive ingredients.

In some instances, certain isomers may actually be deleterious rather than simply inert. For example, the D-enantiomer of thalidomide was a safe and effective sedative when prescribed for the control of morning sickness during pregnancy. However, its L-thalidomide counterpart was discovered to be a potent teratogen.

2.2 Conventional Means of Obtaining Optically Pure Compounds

Methods are available for stereoselective synthesis. For example, a synthetic pathway to optically pure deltamethrin [(1R,3R)-3-(2,2-dibromovinyl)-2,2-dimethyl cyclopropane carboxylic acid] has been developed, but the process is lengthy, complex and costly [Tessier, J., Chem. and Ind., Mar. 9, 1984, p.199]. Moreover, a synthetic scheme capable of producing one specific stereoisomer cannot be applied in a general way to obtain other optically active compounds. What is needed is a generalized approach to the separation of racemic and diastereomeric mixtures produced by non-stereoselective chemical reactions, and a number of approaches have been used.

The terms "racemic mixture" and "diastereomeric mixture" as used herein, refer to mixtures of a first and a second stereoisomer in any proportions, such that the first and second stereoisomers are enantiomers or diastereomers, respectively. Further, it is intended that the term "resolution" as used herein will refer to the transformation of a racemic or diastereomeric mixture, as defined above, into two product mixtures, in each of which the proportions of the two above defined stereoisomers may be different from both the starting racemic or diastereomeric mixture and from each other, the proportion being greater in one and necessarily smaller in the other. The term "resolved" is intended to refer to a quantity of any compound, capable of resolution, which has undergone the process of resolution defined above to yield an optically active product material. Finally, the terms "stereospecific" and "stereoselective" as used herein are synonymous.

A widely used approach has been the selective precipitation of desired stereoisomeric compounds from diastereomeric mixtures. Such diastereomeric mixtures are created by addition of a chiral and optically purified resolving agent to a racemic mixture, which then induces fractional crystallization. Such chiral and optically purified resolving agents form complexes, salts or covalent compounds with the racemic species to be resolved. Said diastereomeric complexes, salts and covalent compounds now possess two or more chiral centers wherein one chiral center in one diastereomer has the same configuration as the corresponding chiral center in another diastereomer, while the diastereomers, other corresponding chiral centers have the opposite configuration. The individual diasteromers have different physical properties (e.g., solubility) and are hence readily separable from one another. For example, Yoshioka et al., [U.S. Pat. No. 3,879,451] treated a mixture of (±)-cis- and (±)-trans-chrysanthemic acids with an optically active aromatic amine and recovered the resulting diastereomeric amine salts of (±)-cis- and (±)-trans-chrysanthemic acids by crystallization. Paven et al., [U.S. Pat. No. 4,257,976] resolved D,L-cis-chrysanthemic acid and D,L-trans-chrysanthemic acid by treating the mixtures with L or D N-methyl-ephedrine to form the corresponding salts, which were then hydrolyzed after isolation to produce the resolved acids. Halmos [U.S. Pat. No. 4,151,198] treated a mixture of N-acyl-D,L(±)-phenylalanine isomers with D(−)-2-(2,5-dimethylbenzylamino)-1-butanol to obtain a crystalline salt, from which N-acyl-L(+)-phenylalanine could be recovered Kameswaran [U.S. Pat. No. 4,454,344] isolated (+) 2-(p-difluoromethoxyphenyl)-3-methylbutanoic acid by treating the racemic acid with an optically active amine. The S(+)-enantiomer of naproxen can be obtained by stereoselective crystallization of a diastereomeric salt formed with an amine resolving agent such as cinchonidine, glucamine, or N-methylglucamine [Harrison, I. T. et al., J. Med. Chem., 13:203 (1970); Felder, E. et al , U.K. Patent Appl. GB2025968A (1980)].

In some cases, a two-step method has been used, as when Dannenberg et al. [U.S. Pat. No. 4,285,884] resolved racemic D,L-alpha-aminocarboxylic acids by first treating the mixture with an aromatic o-hydroxyaldehyde to obtain an azomethine derivative. This derivative was then immediately treated with an optically active amine base to produce a salt which was isolated. By subjecting the salt to acid hydrolysis, the desired alpha-aminocarboxylic acid isomer was obtained.

Regarding captopril, fractional crystallization methods have been noted in resolving captopril, captopril analogues and their precursors, generally based on the use of optically active amines capable of forming diastereomers with the acid precursors of captopril (e.g., 2-methyl-3-thiolpropanoic acid) and its analogues. M. A. Ondetti in U.S. Pat. No. 4,046,889 (Col. 4, lines 52-55); U.S. Pat. No. 4,316,906 (Col. 3, lines 7-11); 4,105,776 (Col. B, lines 59-63) and U.S. Pat. No. 4,154,840 (Col. 8, lines 55-59) discloses that fractional crystallization techniques are available to resolve the racemic precursors of captopril. In U.S. Pat. No. 4,346,045, N. De Heij utilized a fractional crystallization process to isolate D-(−)-S-benzoyl-β-mercaptoisobutyric acid for subsequent conversion to captopril. D-(+)-N-benzyl-α-phenethylamine is used as one of the fractional crystallization reagents (i.e., resolving agents). J. Houbiers in U.S. Pat. No. 4,585,595, also prepared the same captopril precursor. Cinchonidine, D-(−)-2-aminobutanol or a derivative thereof were used as fractional crystallization reagents. Interestingly enough, De Heij also discloses in European Patent Application No. 0,008,831 A1 that cinchonidine is a suitable resolving agent as described in his Dutch Patent Application No. 7,809,121. Also, 1,2-diphenylethylamine and 2-amino-1-butanol have been employed in resolutions (J. Iwao, et al., Jpn. Kokai Tokkyo Koho 79: 151912 (1979); H.-J.-P. Marie. Jpn. Kokai Tokkyo Koho 80: 38386 (1980); N. Ohashi, et al., Jpn. Kokai Tokkyo Koho 81: 7756 (1981)). However, N. Ohashi, et al., in U.S. Pat. No. 4,297,282 noted that racemic-α-methyl-β-acylthiopropanoic acids are not given to fractional crystallization using standard optically active amines such as quinidine, ephedrine, α-methylbenzylamine and brucine (Col. 1, lines 44 to Col. 2, line 2). In addition, even though the use by N. Ohashi, et al. of optically active amines such as 1-(α-naphthyl)-ethylamine and α,β-diphenylethylamine proved to be more successful, it was noted that the procedures were very expensive, cumbersome to effect, and capable of producing only relatively low yields (C. J. Sih, PCT No. WO87/05328 p. 2).

In addition, non-optically active amines have been employed in fractional crystallization resolution steps to prepare captopril. D. H. Naur, et al., J. Pharm. Sci. 73(12): 1843-4 (1984) used dicyclohexylamine to resolve the diastereomers of racemic N-(L-proline)-3-halo-2-methylpropanamide precursor used in a captopril synthesis. Following the isolation of that resolved N-[3-halo-2-methylpropanoyl]proline, the amide can be converted to the corresponding diastereomeric S-protected derivatives of captopril by treating the amide with either a sodium dialkyldithiocarbamate or potassium xanthogenate, as demonstrated by D. K. Kim in U.K. patent No. 2,170,806A. Dicyclohexylamine was also used by I. Castellet-Linan, Spain Patent No. 548154, to resolve the benzoylthio-protected captopril. However, the use of non-optically active amines also incurs an added expense and additional synthetic steps in using the amine.

Consequently, although some of the above procedures successfully resolved racemic or diastereomeric mixtures, not all could be successfully applied to captopril. Moreover, some of these fractional crystallization procedures using optically active reagents did not produce diastereomers with sufficiently different physical properties when applied to captopril and its precursors. Thus, fractional crystallization using such reagents is not always possible.

2.3 Stereospecific Resolutions of Enzyme-Catalyzed Bioconversions of Organic Compounds Various enzymes have been used for bioconversions of assorted organic compounds. Many different classes of enzymes have been used for the resolution of stereoisomers, including hydrolases (especially the lipases, proteases and esterases such as chymotrypsin), lyases and oxidoreductases (e.g., amino acid oxidases and alcohol reductases).

Regarding captopril, enzymatic resolution procedures have been preferably undertaken since there have been problems with fractional crystallization methods. M. Shimazaki, et al., Chem. Pharm. Bull. 30(9): 3139-45 (1982) used a microbiological step developed by Cohen et al., J. Org. Chem. 41, 3505 (1976) to convert isobutyric acid by a bacterial hydroxylation to D-3-hydroxy-2-methylpropanoic acid which was used as a precursor to synthesize captopril. A. Sakimae et al., U.S. Pat. No. 4,629,701 also prepared captopril and captopril analogue precursors represented by the formula,

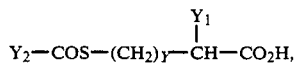

wherein $Y_2$ is an alkyl group, preferably $C_{1-6}$ alkyl group, an aralkyl group, preferably $C_{7-18}$ aralkyl group or an aryl group, preferably $C_{6-26}$ aryl group; $Y_1$ is an alkyl group, preferably $C_{1-6}$ alkyl group; and Y is 1 or 2, by allowing a source containing an enzyme capable of asymmetrically hydrolyzing an ester to act on the ester represented by the formula,

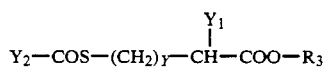

wherein $Y_2$, $Y_1$, and Y have the same meanings as those mentioned above; and $R_3$ is an alkyl group, preferably $C_{1-6}$ alkyl group. In PCT No. WO 87/05328 by C. J. Sih, a microbiological deesterification similar to the one employed by Sakimae was used except that $Y_2$ was either an acyl radical in straight chain, branched chain or cyclic configuration having 1 to about 12 carbon atoms; cycloalkane radicals having 5 to 7 carbon atoms; or benzoyl, naphthoyl, biphenoyl and carbobenzoxy radicals containing substituents such as nitro, halogen, methyl or alkoxy groups on the aromatic ring.

However, the efficiency of these methods is problematic since the enzyme has to be replenished, a cosolvent or emulsifier may have to be employed to facilitate the substrate susceptibility to the enzymatic processing, and some of the enzymes used in these processes are expensive.

Consequently, neither enzymatic resolution nor the previously noted fractional crystallization steps appear to be without certain disadvantages. Therefore, another approach to resolving captopril and its analogues is needed.

3.0 SUMMARY OF THE INVENTION

This invention relates to novel compounds which are thiol protected derivatives of pharmaceutically active inhibitors of Angiotensin-converting enzyme (ACE). The novel compounds are useful in that, as diastereomeric mixtures resulting from non-stereospecific synthesis, they readily undergo a fractional crystallization process referred to herein as "self fractional crystallization," which allows the isolation of a single optically pure derivative of the desired biologically active compound. This derivative is readily converted to the pure pharmaceutically active stereoisomer of the ACE inhibitor by removal of a thiol protecting group.

Intermediates useful in the preparation of these ACE inhibitor derivatives are also novel compounds which are included in the subject matter of this invention.

4.0 BRIEF DESCRIPTION OF THE FIGURES

This invention may be more readily understood by reference to the following detailed description of the invention and figures in which FIG. 1 is a schematic representation of (1) the methods for preparing S-protected captopril and its analogues, (2) the use of the precursors of the S-protected captopril and its analogues and (3) the methods for preparing captopril and its analogues from their S-protected derivatives. In addition, it is noted that the undesired protected diastereomeric amide can be hydrolyzed to isolate the amide's amine for recycling to the coupling (amidization) step.

5.0 DETAILED DESCRIPTION OF THE INVENTION

It is the object of the present invention to cover compositions of matter, wherein the compositions of matter are amide compounds having an S-protected thiol moiety. Also included are intermediates useful in the preparation of these novel S-functionalized amide compounds.

The amide compounds which are the primary subject matter of this invention contain two chiral centers wherein one of the chiral centers is located alpha to the carboxyl carbon in the thiol alkanoyl segment of the amide and the other chiral center is alpha to the nitrogen which forms the amide. Consequently, the compounds may be produced as mixtures of diastereomers. The compounds are useful in that they directly, without further chemical modification, undergo fractional crystallization to allow separation of their component diastereomers. This property of the subject compounds is described herein as "self-fractional crystallization".

Self-fractional crystallization is to be distinguished from the usual practice of fractional crystallization to resolve stereoisomers whereby the desired stereoisomer is separated as a diastereomeric derivative (for example, resolution of a racemic mixture of a carboxylic acid by fractional crystallization of a diastereomeric mixture of salts formed between the former and an optically active amine). This usual practice requires regeneration of the underivatized compound and recovery of the amine "resolving agent". In the present invention it is an unexpected property of the subject compounds that they undergo self-fractional crystallization with sufficiently high selectivity and efficiency that the S-protected drug precursor requires no further stereochemical purification. This self-fractional crystallization behavior is attributed to the physical properties resulting from the novel thiol protecting group.

Specifically, racemic S-functionalized carboxylic acid compounds are covered by this invention, as are the S-functionalized amide compounds which result from their reactions with alpha-amino acids or alpha-amino acid derivatives. Said S-functionalized amide compounds may undergo self-fractional crystallization and be further converted by removal of the thiol protecting group to the desired single optical isomer of the desired compound. As a specific example of the utility of the claimed compounds, reaction of the claimed racemic S-functionalized carboxylic acid compound (after conversion to a suitable acylating agent) with L-proline results in formation of a diastereomeric mixture of amide compounds which undergoes self-fractional crystallization and is further converted by de-protection to captopril.

Embodiments of this invention, therefore, pertain to compositions of matter which are capable of undergoing self-fractional crystallization and which, by further chemical processing, are readily converted to the stereochemically enriched form of biologically active compounds. Methods of making such novel compounds and methods of converting them to biologically active agents (e.g. captopril and its analogues) are described herein.

5.1 Novel Compositions of Matter Pertaining to Derivatives and Precursors of Captopril and its Analogues

5.1.1 Thiol-Protected Derivatives of Captopril and its Analogues

Regarding the thiol-protected derivatives of captopril and its analogues, which are embodied in this invention, the importance of these compositions of matter resides in the protecting group's facilitation of the compositions' self-fractional crystallization characteristics. Consequently, a diastereomeric mixture of the thiol-protected derivatives is separable to the individual diastereomeric species, one of which is then converted to the corresponding diastereomeric de-protected captopril species and its analogues by a deprotection step.

Regarding heterocyclic amine compounds or amine segments in cyclic amides herein represented by the formulae

wherein $R_5$ is selected from the group consisting of hydrogen, lower alkyl, lower alkoxy, phenoxy, hydroxy, thiol, alkylthio, halide, phenyl and substituted phenyl, and p is 2, 3, or 4; and

wherein R is selected from the group consisting of hydroxy, amino and lower alkoxy, $R_3$ is selected from the group consisting of hydrogen, lower alkyl, lower alkoxy, phenoxy, hydroxy, thiol, alkylthio, arylthio, halide, phenyl and substituted phenyl, and m is 2, 3, or 4, both of the formulae represent rings ranging in sizes from four to six. More specifically, where m is 3 regarding formula II it corresponds to the substituent group $R_7$ described later herein as being selected from the group consisting of L-proline (where R is hydroxyl and $R_3$ is hydrogen) and substituted L-proline selected from the group consisting of 4S-(phenylthio)-L-proline, 4S-hydroxy L-proline, lower alkyl ester of L-proline and amide of L-proline. In addition, the $R_5$ and $R_3$ groups are each represented as such to note that they can substitute for any methylene ($-CH_2-$) hydrogen(s) of the ring. The substitutions pertain to those replacements which either provide a heterocyclic amine which is non-optically active or which replacement involves a single stereoconfiguration at that chiral carbon which is the site of substitution. Examples of the former are geminal substitutions or those which provide meso compounds (i.e., having a plane of symmetry). An example of the latter is provided by substituted L-proline wherein the substituent group $R_3$ is 4S-(phenylthio).

Generally stated, the preferred embodiment of this invention comprises novel compositions of matter pertaining to a compound of the formula III

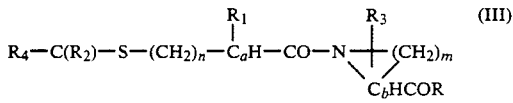

wherein R is selected from the group consisting of hydroxy, amino and lower alkoxy; $R_1$ is selected from the group consisting of lower alkyl, lower alkoxy, hydroxy, halide, phenyl and substituted phenyl; $R_2$ is selected from the group consisting of O, S and imino; $R_3$ is selected from the group consisting of hydrogen, lower alkyl, lower alkoxy, phenoxy, hydroxy, thiol, alkylthio, arylthio, halide, phenyl and substituted phenyl; $R_4$ is a cyclic secondary amino; m is 2, 3 or 4; $C_a$ has an S or R configuration; $C_b$ has a D or L configuration; n is 1, 2 or 3; and basic salts thereof.

The embodiments of the invention also encompass the compound of formula III wherein said cyclic secondary amino has the formula I as described above; said $R_2$ is an imino which has the formula $NR_6$ wherein $R_6$ is selected from the group consisting of hydrogen, hydroxy, lower alkoxy, lower alkyl, phenyl and substituted phenyl; said phenyl substituent is selected from the group consisting of halide, lower alkyl, hydroxy and lower alkoxy; and said lower alkoxy and lower alkyl groups have up to seven carbon Three further embodiments of this invention include the compound of the formula III:

1) wherein R is hydroxy, $R_1$ is lower alkyl wherein said lower alkyl is methyl, $R_2$ is S, $R_3$ is hydrogen, 4S-hydroxy or 4S-phenylthio, n is 1, m is 3, $R_4$ is a cyclic secondary amino of the formula I above wherein $R_5$ is hydrogen and p is 3, and $C_b$ has an L configuration;

2) wherein R is lower alkoxy wherein said lower alkoxy is methoxy or t-butoxy, $R_1$ is lower alkyl wherein said lower alkyl is methyl, $R_2$ is S, $R_3$ is hydrogen, 4S-hydroxy or 4S-phenylthio, n is 1, m is 3, $R_4$ is a cyclic secondary amino of the formula of I above wherein $R_5$ is hydrogen and p is 3, and $C_b$ has an L configuration; and 3) wherein R is lower alkoxy wherein said lower alkoxy is methoxy, $R_1$ is lower alkyl wherein said lower alkyl is methyl, $R_2$ is O, $R_3$ is hydrogen, 4S-hydroxy or 4S-phenylthio, n is 1, m is 3, $R_4$ is a cyclic secondary amino of the formula of I above, wherein $R_5$ is hydrogen and p is 3, and $C_b$ has an L configuration.

Another embodiment of this invention comprises novel compositions of matter pertaining to a compound of the formula IV

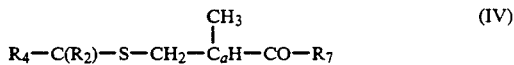

and basic salts thereof wherein the substituents are defined as above.

Further embodiments of this invention include the compound of the formula IV:

1) wherein $R_2$ is S, $R_4$ is a cyclic secondary amino of formula I above wherein $R_5$ is hydrogen and p is 3, and $R_7$ is a) L-proline or b) substituted L-(proline) wherein the substituted L-proline is
  (i) 4S-(phenylthio)proline,
  (ii) 4S-hydroxyproline or
  (iii) lower alkyl ester of L-proline wherein said lower alkyl ester of L-proline is methyl ester of L-proline or t-butyl ester of L-proline; and 2) wherein $R_2$ is O, $R_4$ is a cyclic secondary amino of formula I above wherein $R_5$ is hydrogen and p is 3, and $R_7$ is substituted L-proline wherein said substituted L-proline is lower alkyl ester of L-proline wherein said lower alkyl ester of L-proline is methyl ester of L-proline.

More particularly, another preferred embodiment of this invention comprises novel compositions of matter pertaining to a compound of the formula V

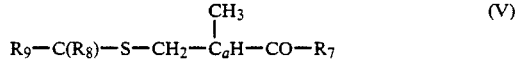

wherein $R_8$ is selected from the group consisting of O and S; $R_9$ is pyrrolidino; and basic salts thereof wherein all the other substituents are defined as above.

Further embodiments of this invention include a compound:

1) wherein $R_8$ is S, and $R_7$ is
  a) L-proline or
  b) substituted L-proline wherein the substituted L-proline is
    (i) 4S-(phenylthio)-L-proline
    (ii) 4S-hydroxy-L-proline or
    (iii) lower alkyl ester of L-proline wherein said lower alkyl ester of L-proline is methyl ester of L-proline or t-butyl ester of L-proline; and 2) wherein $R_2$ is O, and $R_7$ is substituted L-proline wherein said substituted L-proline is lower alkyl ester of L-proline wherein said lower alkyl ester of L-proline is methyl ester of L-proline.

5.1.2 Precursors of the Thiol-Protected Derivatives of Captopril and its Analogues Regarding the significance of the precursors of the S-protected derivatives of captopril and its analogues, the S-protected precursor provides a novel and simple substrate for forming S-protected derivatives (thiol-protected captopril and its analogues) which undergo self-fractional crystallization upon their formation from that In addition, it is noted that the amidization of the precursor with optically active amines other than proline or its analogues is useful for forming amides which also undergo self-fractional crystallization to separate diastereomeric amide species. More specifically, these resulting individual diastereomeric amides are separately hydrolyzable to the corresponding optically resolved amine species. Consequently, the precursor has utility for preparing individual diastereomeric amide species of which it is part.

Another preferred embodiment of this invention comprises novel compositions of matter pertaining to a compound of the formula VI

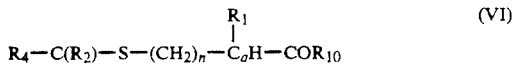

wherein $R_{10}$ is selected from the group consisting of lower alkoxy or hydroxy, and basic salts thereof wherein the other substituents are defined as above.

Further embodiments of this invention include the compound of the formula VI wherein: $R_1$ is lower alkyl wherein said lower alkyl is methyl, $R_2$ is S, n is 1, $R_4$ is a cyclic secondary amino of the formula I as defined above wherein $R_5$ is hydrogen and p is 3, and $R_{10}$ is hydroxy.

Another embodiment of this invention comprises novel compositions of matter pertaining to a compound of the formula VII

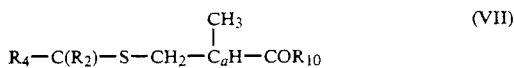

and basic salts thereof wherein the substituent groups are defined above.

Further embodiments of this invention include the compound of the formula VII wherein: $R_2$ is S, $R_4$ is a cyclic secondary amino of formula I defined above wherein $R_5$ is hydrogen and p is 3, and $R_{10}$ is hydroxy.

More specifically, the embodiment of this invention also comprises novel compositions of matter pertaining to a compound of the formula VIII

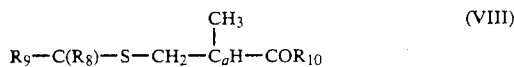

and basic salts thereof wherein the substituent groups are defined above.

Further embodiments of this invention include a compound of the formula VIII wherein: $R_8$ is S and $R_{10}$ is hydroxy.

5.2 Methods for Preparing Captopril and its Analogues, Their Thiol-Protected Derivatives and Precursors

5.2.1 Preparations of Thiol-Protected Derivatives of Captopril and its Analogues The production of useful derivatives of captopril and its analogues which undergo self-fractional crystallization whereby the diastereomeric species are convertable to captopril and its analogues is also described. As noted, the derivatives are useful since they are incorporated with the S-protecting groups which make them susceptible to self-fractional crystallization. Furthermore, such derivatives can be de-protected to form desirable diastereomeric amides, or hydrolyzed to form diastereomeric amines (FIG. 1).

To prepare the novel compositions of matter an assortment of methods were employed. In the following methods to prepare derivatized captopril and its analogues, the designation of the substituents is the same as noted in discussion regarding genus formula except where noted.

One method for making a compound of the following formula IX

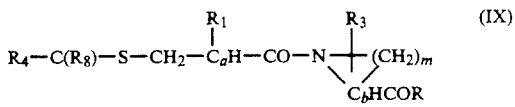

and basic salts thereof wherein all of the substituents are defined above, comprises:

a) reacting the compound of the formula X

with a compound of the formula $R_8\!\!=\!\!C\!\!=\!\!S$ (XI) and a cyclic secondary amine to form the compound of the formula XII

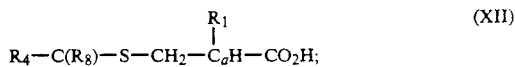

wherein the substituents in the compounds are defined above;

b) converting said formed compound of the formula XII of step a) to an acylating agent by reacting it, for example, with the acid chloride of an inorganic acid;

c) reacting said formed acylating agent of step b) with a compound of the formula II to form said compound of the formula IX; and d) isolating said compound of the formula IX.

A method for making a compound of the following formula XIII

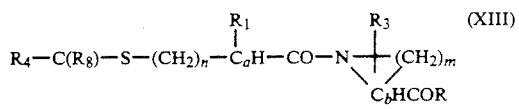

and basic salts thereof wherein all of the substituents are defined above, comprises:

a) reacting the compound of the formula XIV

wherein L is a leaving group, with a compound of the formula XI and a cyclic secondary amine to form the compound of the formula XV

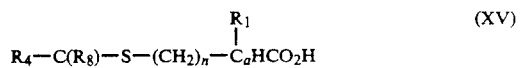

wherein the other substituents in the compounds are defined above;

b) converting said compound of the formula XV of step a) to an acylating agent by reacting it, for example, with the acid chloride of an inorganic acid;

c) reacting said formed acylating agent of step b) with a compound of the formula II to form said compound of the formula XIII; and d) isolating said compound of the formula XIII.

A method for making a compound of the following formula XVI

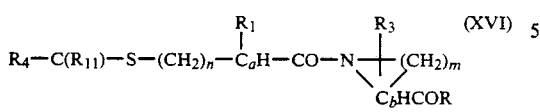

and basic salts thereof, wherein $R_{11}$ is imino, and the other substituents are defined above, comprises:

a) reacting the compound of the formula XIV and a compound of the formula $R_4C(S)NHR_6$ (XVII) to form the compound of the formula XVIII

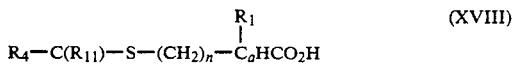

wherein the substituents in the compounds are defined above;

b) converting said compound of the formula XVIII of step a) to an acylating agent by reacting it, for example, with the acid chloride of an inorganic acid;

c) reacting said formed acylating agent of step b) with a compound of the formula II to form said compound of the formula XVI; and d) isolating said compound of the formula XVI.

A further method for making a compound of the following formula IX

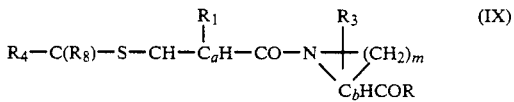

and basic salts thereof wherein all of the substituent groups are defined above, comprises:

a) reacting the compound of the formula XIX $$H_2CC_aR_1COR_{12} \qquad (XIX)$$

wherein $R_{12}$ is lower alkoxy, with a compound of the formula XI and a cyclic secondary amine to form the compound of the formula XX

wherein the other substituents in the compounds are defined above;

b) hydrolyzing said compound of the formula XX whereby said $R_{12}$ group is replaced by a hydroxyl group to form a compound of the formula XII;

c) converting said formed compound of the formula XII of step b) to an acylating agent by reacting it with, for example, the acid chloride of an inorganic acid;

d) reacting said formed acylating agent of step c) with a compound of the formula II to form said compound of the formula IX; and e) isolating said compound of the formula IX.

Finally, an additional method for making a compound of the following formula XVI

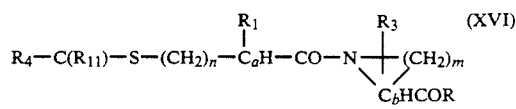

and basic salts thereof wherein all of the substituents are defined above, comprises:

a) reacting the compound of the formula XXI $$L(CH_2)_nC_aHR_1COR_{12} \qquad (XXI)$$

and a compound of the formula XVII to form the compound of the formula XXII

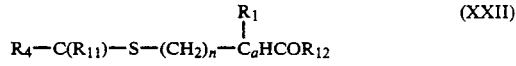

wherein the substituents in the compounds are defined above;

b) hydrolyzing said compound of the formula XXII whereby said $R_{12}$ group is replaced by a hydroxyl group to form a compound of the formula XVIII;

c) converting said compound of the formula XVIII of step b) to an acylating agent by reacting it, for example, with the acid chloride of an inorganic acid;

d) reacting said formed acylating agent of step c) with a compound of the formula II to form said compound of the formula XVI; and e) isolating said compound of the formula XVI.

With regard to the prior noted methods for preparing the compounds which comprise compound III, the methods also pertain to the preparation of compounds wherein the protecting group portion of the compound is variable as noted regarding the compositions of matter, whereas the alkanoyl and amino portions of the amide compound are limited respectively to 2-methyl-3-thiopropanoyl and to L-proline and substituted L-proline, including but not limited to the case wherein the substituted L-proline is 4S-(phenylthio)-L-proline. In addition, the methods are useful in the situation wherein the protecting group is limited to pyrrolidinocarbonyl or pyrrolidinothioxomethyl, and the thioalkylcarboxamide portion of the compound is limited as just noted.

Compound III may also be prepared by alternating the preparative sequences noted in prior methods. Here the initial step again necessitates condensing the carboxylic acid compounds of step (a) of the prior noted methods with an amine using known methods to produce an amide. For example, one such method involves reacting the carboxylic acid compounds of step (a) with the acid halide of an inorganic acid to convert the carboxylic acid to an acylating agent. However, the order of subsequent reaction steps can be changed. In these alternative methods, the formed acylating agent is then subjected to an amidization reaction as noted in the prior noted preparative methods. Once the amide is formed, the carboxylic acid portion of the amide undergoes reaction steps as noted in the prior discussed preparative methods whereby the S-functionalized thiol group is incorporated in the carboxylic acid portion of the amide to form compound III.

More specifically, as an example, a derivative and precursor of captopril were prepared as follows. The S-protected 2-methyl-3-thiopropanoic acid corresponding to formula VII is formed where pyrrolidine, carbon disulfide and methacrylic acid are allowed to react— preferably in equimolar amounts—either with, or without a solvent present. Typically, the reactants are dissolved in a solvent, for example, 2-propanol or ethyl acetate, in the amounts of about 5 to about 40 weight percent. This solution is then either refluxed for about 1 to about 10 hours or kept at room temperature for from about 1 to about 5 days. The desired product either crystallizes spontaneously from solution or is induced to crystallize by the addition of a non-solvent. After chilling to about $-5°$ C. to about $15°$ C. for about 1 to about 12 hours the S-protected 2-methyl-3-thiopropanoic acid precursor is isolated by filtration or centrifugation, washed with a small amount of crystallization solvent and air dried or dried in an oven or vacuum oven. This material is pure enough to be used in the coupling reaction with L-proline or another nucleophile to form the S-protected 2-methyl-3-thiopropanoic acid. For such a reaction the compound is dissolved in methylene chloride or another suitable solvent at a concentration of about 2 to about 15 weight percent and is treated with about 0.9 to about 1.1 equivalent of an inorganic acid chloride, typically thionyl chloride at about $-5°$ C. to about $25°$ C. After about 10 minutes to about 1 hour L-proline or another nucleophile is added followed by the addition of about 2 to about 5 equivalents of an organic base, for example, pyridine at a temperature of from about $-5°$ C. to about $25°$ C. After about 0.5 to about 2 hours, the solution is washed with aqueous acid to remove the base. The product is (i) crystallized directly from solution, (ii) induced to crystallize by addition of a non-solvent, (iii) collected by evaporating the reaction solvent followed by dissolving the product in a solvent from which it can be recrystallized, or (iv) crystallized by a combination of the above.

5.2.2. Preparations of Precursors of Thiol-Protected Derivatives of Captopril and its Analogues Described herein are also methods that relate to the production of a useful precursor for combining with an amine whereby the resulting amide undergoes self-fractional crystallization. The reaction of the precursor with carboxyl-substituted heterocyclic amine compounds of the formula II and more specifically proline or substituted proline, whereby the protected thiol derivatives of captopril and its analogues are easily prepared, is of particular interest. In particular, the precursor is useful since it is incorporated with the S-functionalized substituent which facilitates the previously noted derivative's susceptibility to self-fractional crystallization upon its formation from that precursor.

In the following methods for preparation of the captopril precursors and their analogues, the designation of the substituents is the same as noted in the discussion of Section 5.1.1 and the discussion regarding genus formula except where noted. More limited descriptions of the compounds are also described therein.

A method for preparing a precursor which is useful for preparing derivatives of captopril and its analogues pertains to a method for making a compound of the formula XXIII

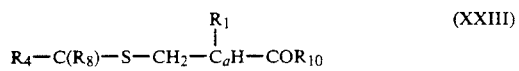

wherein the substituent groups are defined above. The method comprises:

a) reacting the compound of the formula XXIV

with a compound of the formula XI and a cyclic secondary amine to form the compound of the formula XXIII wherein the substituent groups in the compounds are defined above; and b) isolating said compound of the formula XXIII.

Another method for preparing a precursor which is useful for preparing derivatives of captopril and its analogues pertains to a method for making a compound of the formula XXV

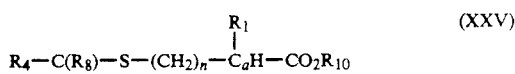

wherein the substituents are defined above. The method comprises:

a) reacting the compound of the formula XXVI

with a compound of the formula XI and a cyclic secondary amine to form the compound of the formula XXV wherein the substituent groups in the compounds are defined above; and b) isolating said compound of the formula XXV.

Another method for preparing a precursor which is useful for preparing derivatives of captopril and its analogues pertains to a method for making a compound of the formula XXVII

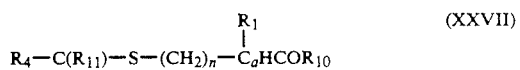

wherein the substituent groups are defined above. The method comprises:

a) reacting the compound of the formula XXVI and a compound of the formula XVII to form the compound of the formula XXVII wherein the substituent groups in the compound are defined above; and b) isolating said compound of the formula XXVII.

With regard to the methods for preparing these precursor compounds, the methods also relate to the preparation of compounds wherein the protecting group portion of the compound is variable as noted whereas the thioalkanoyl portion of the compound is limited to 2-methyl-3-thiopropanoyl. In addition, the methods are useful in the situation wherein the protecting group is limited to pyrrolidinocarbonyl or pyrrolidinothioxomethyl, and the thioalkanoyl portion of the compound is limited as noted.

5.2.3 Preparations of Captopril and its Analogues From Their Thiol-Protected Derivatives The preparation of captopril and captopril analogues as the racemic mixture or chiral species is also described herein. The desired racemic species is obtained by affecting the removal of the thiol protecting group. Of particular significance regarding the described method is that the precursor can be separated as a pure diastereomer by its self-fractional crystallization, and subsequently treated to remove the thiol protecting group to obtain captopril or a captopril analogue. Specific details regarding the preparation of captopril and its analogues are exemplified by the following procedures used in preparing captopril.

The preparation of a mixture of diastereomers is accomplished starting from non-optically active raw materials that condense to form a racemic mixture of S-protected 2-methyl-3-thiopropanoic acid. Such syntheses of S-protected captopril and its analogues are noted previously herein. This material is then coupled with L-proline to form S-protected captopril as a mixture of diastereomers. This can be conducted by two general processes. One involves isolation of the racemic acid precursor from one set of solvents (e.g. isopropanol/water) and subsequent coupling to L-proline in another solvent (e.g. methylene chloride). The other general approach conducts both reactions in one solvent (e.g., ethyl acetate) without precursor isolation.

When L-proline is coupled with the S-protected 2-methyl-3-thiopropanoic acid, diastereomers of S-protected captopril are formed. A solution comprised of these diastereomers having (S,S) and (R,S) configurations is prepared in the desired crystallization solvent (e.g. ethyl acetate), at a concentration of about 6 to about 35%, by solvent exchange from methylene chloride or directly from the coupling reaction after base (pyridine) removal. Crystallization of the desired diastereomer is accomplished by reducing the temperature from about −20° C. to about 10° C., and either adding non-solvent, removing solvent, or some combination thereof.

The (S,S) diastereomer will crystallize from the solution while the remaining mother liquor contains predominately the other diastereomer. The solid can be collected by filtration or centrifugation. After washing with said crystallizing solvent, the solid is further converted by de-protection to captopril while the filtrate is sent for proline recovery and recycling. The solvent-wet crystals, isolated from the above fractional crystallization, represent 40 to 49% recovery of the (S,S) diastereomer of the protected captopril (or captopril analog).

Captopril and captopril analogs can be produced from their S-protected derivatives by direct hydrolysis of the S-protected derivative. The S-protected material is first dissolved in a concentrated aqueous solution of an alkaline metal hydroxide—preferably with the hydroxide at a concentration from about 5 wt % to about 25 wt %—to yield a solution containing about 5 wt % to about 25 wt % of the S-protected captopril derivative. A preferred hydroxide solution is aqueous potassium hydroxide. This solution is then refluxed for from about 1 hour to about 24 hours, preferably under an inert gas (e.g., nitrogen) atmosphere. After cooling, the solution is acidified to a pH of about 0 to about 3, and then it is extracted with an organic solvent. Suitable organic solvents include methylene chloride, ethyl acetate, and chloroform. Finally, the solvent is removed or concentrated, and the desired (S, S) diastereomer of captopril or captopril analog is isolated by crystallization, chromatography, or yet another standard purification method.

The filtrate from the asymmetric crystallization step contains predominately the (R,S) diastereomer of the S-protected captopril. The crystallizing solvent is evaporated and replaced with a solution of a strong acid (e.g., hydrochloric acid). This mixture is heated to reflux for about 1 to about 10 hours to hydrolyze the amide bond. The proline is then recovered by conventional means and recycled as the free amino acid or its hydrochloride salt.

One method which is useful in preparing captopril and its analogues pertains to a method for the production of a compound of the formula XXVIII

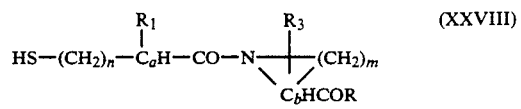

and basic salts thereof, wherein the substituent groups are defined above, comprises:

a) preparing a mixture of diastereomers of a compound of formula III wherein the diastereomeric mixture contains two stereoisomers which have the same configuration at $C_b$ and opposite configurations at $C_a$;

b) preparing a solution of said mixture of said diastereomers in a solvent;

c) allowing predominantly one diastereomer of said mixture to crystallize from the resulting solution, said solution becoming enriched in the other diastereomer;

d) separating said crystallized and resolved diastereomer from said resulting solution containing said other resolved diastereomer;

e) removing the thiol protecting substituent of the formula XXIX

wherein the substituent groups are defined above, from either of said separated and resolved diastereomers, to form either resolved diastereomer of formula XXVIII; and f) isolating either resolved diastereomer of formula XXVIII;

whereby either resolved diastereomer of the compound of formula XXVIII is obtained.

Another method which is useful in preparing captopril and its analogues pertains to a method for the production of a compound of the formula XXX

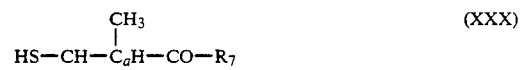

and basic salts thereof, wherein the substituent groups are defined above, comprises:

a) preparing a mixture of diastereomers of a compound of formula IV wherein the diastereomeric mixture contains two stereoisomers which have opposite configurations at $C_a$; and basic salts thereof;

b) preparing a solution of said mixture of said diastereomers in a solvent;

c) allowing predominantly one diastereomer of said mixture to crystallize from the resulting solution, said solution becoming enriched in the other diastereomer;

d) separating said crystallized and resolved diastereomer from said resulting solution containing said other resolved diastereomer;

e) removing the thiol protecting substituent of the formula XXIX from either of said separated and resolved diastereomers, to form either resolved diastereomer of formula XXX, and f) isolating either resolved diastereomer of formula XXX, whereby either resolved diastereomer of the compound of formula XXX is obtained.

Another method which is useful in preparing captopril and its analogues pertains to a method for the production of a compound of the formula XXX and basic salts thereof, wherein all of the substituent groups are defined above, comprises:

a) preparing a mixture of diastereomers of a compound of formula V wherein the diastereomeric mixture contains two stereoisomers which have opposite configurations at $C_a$; and basic salts thereof;

b) preparing a solution of said mixture of said diastereomers in a solvent;

c) allowing predominantly one diastereomer of said mixture to crystallize from the resulting solution, said solution becoming enriched in the other diastereomer;

d) separating said crystallized and resolved diastereomer from said resulting solution containing said other resolved diastereomer;

e) removing the thiol protecting substituent of the formula XXXI $$R_9-C- \quad (XXXI)$$

from either of said separated and resolved diastereomers, to form either resolved diastereomer of formula XXX; and f) isolating either resolved diastereomer of formula XXX;

whereby either resolved diastereomer of the compound of formula XXX is obtained.

6.0 EXAMPLES

6.1 Preparation of 2-Methyl-3-(S-pyrrolidinothioxomethyl)thiopropanoic Acid (XXXII)

8.6 g (0.1 m) of methacrylic acid was added to 50 ml of isopropyl alcohol, cooled on ice, and treated with stirring, with 7.1 g (8.3 ml, 0.1 m) of pyrrolidine. This mixture was, in turn, treated under the same conditions with 7.6 g (6.00 ml, 0.1 m) of carbon disulfide. The solution was then placed in an oil bath at 110° C. and refluxed for 2.5 hours. The heat was removed and 50 ml of water was added. Upon cooling, the product crystallized as a white solid. This was collected by filtration, washed two times with cold 50/50 $H_2/O$ isopropyl alcohol and dried to yield 17 g of material at 73% yield and with a melting point of 135°-136° C.

6.2 Preparation of N-[2-Methyl-3-(S-pyrrolidinothioxomethyl)thiopropanoyl] L-Proline (XXXIII) Using Two Reaction Solvents A solution of the compound of formula XXXII (750 g, 3.21 m) was prepared in 4.0 l of dichloromethane and was chilled in an ice bath to 15° C. Thionyl chloride (382 g, 234.5 ml, 3.21 m) was run into this stirred solution over the course of 15 minutes. The slurry thus formed was stirred on ice for ½ hour, after which L-proline (370 g, 3.21 m) was added. The pyridine (763 g) was dripped in over a 45 minute period, the temperature being kept at less than 25° C. by use of an ice bath. Upon complete addition of the pyridine, the solution was stirred at room temperature for 1 hour. The resulting solution was washed 2 times with dilute HCl to remove pyridine. The dichloromethane solution was diluted with 4 liters of ethyl acetate and solvent was distilled from the flask. Water which was present was removed as the azeotrope with dichloromethane. Distillation was continued until the vapor temperature reached 65° C., during which time product began to crystallize. After cooling to room temperature overnight, the solid was isolated by filtration to give 420 gm of a white product with a rotation of −1.375° (c=1/ethanol). This material was recrystallized from 1.6 liters of 2-methoxyethanol to provide 350 g of pure product with a rotation of −1.443° (c=1/ethanol); the melting point of the material was 190°-191° C.

6.3 Preparation of N-[2-Methyl-3-(S-pyrrolidinothioxomethyl)thiopropanoyl] L-Proline (XXXIII) Using A Single Reaction Solvent 17.2 g (16.94 ml, 0.2 m) of methacrylic acid was added to 0.3 l of ethyl acetate and was stirred as pyrrolidine (16.6 ml, 0.2 m) was slowly added. Then to the stirred solution was slowly added carbon disulfide (12.0 ml, 0.2 m). The mix became warm as a solid began to precipitate. The mix was refluxed for 2.5 hours to give a pale yellow solution. The solution was cooled to 25° and then treated with thionyl chloride (23.8 g, 14.6 ml, 0.2 m) with stirring. After 15 minutes, the slurry was cooled in ice. With stirring, L-proline (23 g, 0.2 m) was added followed by the dropwise addition of 20 ml of pyridine. After ½ hour 0.1 l $H_2O$ and 20 ml concentrated HCl were added, and the mixture was stirred 5 minutes and cooled on ice, this causing the product to precipitate as a white powder. The yield was 8.5 g (26%) and the rotation was −1.003° (C=1/ethanol. Further cooling of the filtrates gave an additional 8.7 g of the product which had a rotation of −0.982° (C=1/ethanol).

6.4 Preparation of Methyl Ester of N-[2-Methyl-3-(S-pyrrolidinothioxomethyl)thiopropanoyl] L-Proline (XXXIV) Using Esterified Reactant 7.0 gm (0.03 m) of the protected mercaptoisobutyric acid from above (XXIX) was dissolved in 100 ml of methylene chloride, and was treated with thionyl chloride (3.6 g, 2.2 ml, 0.03 m). After 15 minutes the slurry was cooled to 0° C., and L-proline methyl ester hydrochloride (5.0 g, 0.03 m) was added with stirring. To this stirred mixture, pyridine (10 ml) was slowly dripped in with stirring. After 1 hour the pale yellow solution was diluted with 200 ml of ethyl acetate and this solution was extracted with water (2×100 ml). After drying over magnesium sulfate, the solvents were stripped to give an oil which solidified upon cooling. This solid was recrystallized from isopropyl alcohol to yield 3.0 g (29.0%) of white crystals. The melting point of the product was 124°-125° C. and its rotation was −1.526° (C=1/ethanol).

6.5 Preparation of Methyl Ester of N-[2-methyl-3-(S-pyrrolidinothioxomethyl)thiopropanoyl] L-Proline (XXXIV) By Esterification Step The resolved, protected captopril derivative (11.0 g, 0.033 m) from above (XXXIII) was dissolved in 250 ml of methanol. This solution was treated with gaseous hydrogen chloride and left overnight. The excess methanol was stripped and the residue was poured into water. The white solid thus formed was filtered, and washed well with water. The damp filter cake was recrystallized from isopropyl alcohol to yield 9.3 g (81.0%) of white crystals. The product's melting point was 124°-125° C. and its rotation was −1.493° (C=1/ethanol).

6.6 Preparation of the t-Butyl Ester of N-[2-Methyl-3-(S-pyrrolidinothioxomethyl)thiopropanoyl] L-Proline (XXXV)

15.3 gm of the protected captopril derivative from above (XXXIII) was mixed with 150 ml of methylene chloride and 1.0 ml of methanesulfonic acid. This was cooled in dry ice/acetone and 50 ml of liquid isobutylene was added. The bottle was stoppered and then shaken on a Parr apparatus for 48 hours. The resulting clear solution was cooled on dry ice/acetone before opening. The contents were poured into 1.0N sodium hydroxide and the organic material which separated was taken into diethyl ether. After drying over magnesium sulfate, the solvents were stripped to give a white solid. This was dissolved in a small amount of methylene chloride. Hexane was added to the cloud point. Upon cooling and scratching, 13.5 g (75.9%) of the ester crystallized as a white powder. The rotation was −1.430° (C=1/ethanol) and its melting point was 128°-129° C.

6.7 Preparation of Methyl Ester of N-[2-Methyl-3-(S-pyrrolidinocarbonyl)thiopropanoyl] L-Proline (XXXVI)

3.44 g (0.01 m) of (XXXIV) was treated with dimethyl sulfate (1.26 g, 0.01 m, 0.95 ml) and was heated in an oil bath at 90° C. for 1 hour. The clear product was dissolved in 25 ml of 4:1 $H_2O$ HCl and was stirred at room temperature for 15 minutes. This solution was saturated with NaCl to precipitate some starting material which was extracted into ethyl acetate. The aqueous layer was treated with concentrated $NH_4OH$ to a pH of 11-12. After 5 minutes the precipitated oil was taken into ethyl acetate, dried and stripped to give 2.5 g of a clear oil. This was dissolved in 10 ml ethyl acetate and treated with hexane to the cloud point. Upon cooling, a yield of 1.5 g of a white solid crystallized from the solution. The melting point of the product is 90°-91° C. and its rotation −1.323° (C=1/ethanol).

6.8 Preparation of N-[2-Methyl-3-(thiopropanoyl] L-Proline (Captopril) (XXXVII)

A solution of potassium hydroxide (70.0 g, 1.25 m) in 250 ml of water was prepared, and de-oxygenated with nitrogen. This solution was stirred as 50 gm (0.15 m) of the resolved protected captopril compound (XXXIII) (α=−1.428° c=1/ethanol) was added. The resulting solution was kept under nitrogen as it was brought to reflux. After 2 hours, the solution was cooled to room temperature and then placed in an ice bath. Concentrated HCl (about 80 to about 85 ml) was dripped in with stirring causing the evolution of $CO_2$ and $H_2S$. When the solution became acidic (pH about 1 to about 2) a white precipitate formed. This precipitate was removed by filtration, and the filtrates were extracted four times with about 150 ml portions of methylene chloride. The extracts were combined, dried over magnesium sulfate and stripped to provide a clear oil in a yield of 31 gm. HPLC analysis showed the oil to be about 75% captopril wherein the overall chemical yield was 23.3 gm (71%).

A portion of the crude product was purified by chromatography on silica gel using ethyl acetate (94)/methanol (5)/acetic acid (1) as the eluent. The fractions containing captopril were pooled and evaporated to provide captopril as an oil. This oil was solidified by trituration in diethyl ether to provide purified captopril. Its rotation was −1.281° (c=1/ethanol).

The present invention is not intended to be limited in scope by the above examples concerning the composition of matter and the method for making the ycomposition of matter, described herein, since each is intended merely as an illustration of the invention. In addition, any method which is functionally equivalent to those set forth herein is intended to be within the scope of the invention. Indeed various modifications of the invention, in addition to those shown and described herein, will become apparent to those skilled in the art from the foregoing description and accompanying specification. Such modifications are intended to fall within the scope of the appended claims.

I claim:

1. A self-fractional crystallizing compound of formula III

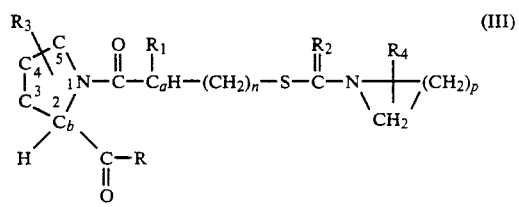

wherein:

R is hydroxy, —$NH_2$ or lower alkoxy;

$R_1$ is lower alkyl, lower alkoxy, hydroxy, halide, phenyl or substituted phenyl wherein the substituents on the phenyl are selected from the group consisting of halide, lower alkyl, lower alkoxy, and hydroxy;

$R_2$ is O, S or NH;

$R_3$ is present or absent and, if present, is lower alkyl, lower alkoxy, phenoxy, hydroxy, thiol, alkylthio, arylthio, wherein the aryl group of the arylthio contains 6-26 carbons, halide, phenyl or substituted phenyl where the substituents on the phenyl are selected from the group consisting of halide, lower alkyl, hydroxy and lower alkoxy, and wherein $R_3$ can be substituted for any methylene (—$CH_2$—) hydrogen(s) of the ring;

$R_4$ is present or absent and, if present, is lower alkyl, lower alkoxy, phenoxy, hydroxy, thiol, alkylthio, arylthio, wherein the aryl group contains 6-26 carbon atoms, halide, phenyl or substituted phenyl where the substituents on the phenyl are selected from the group consisting of halide, lower alkyl, hydroxy, lower alkoxy, and wherein $R_4$ can be substituted for any methylene (—$CH_2$—) hydrogen(s) of the ring;

$C_a$ has an S or R configuration;

$C_b$ has a D or L configuration;

n is 1, 2 or 3;

p is 3; and basic salts thereof.

2. The compound of claim 1 wherein R is hydroxy, $NH_2$, methoxy or butoxy; $R_1$ is methyl; $R_2$ is S or O; $R_3$ is present or absent and if present, is 4S-hydroxy or 4S-phenylthio; $R_4$ is absent; n is 1; $C_a$ has an S or R configuration and $C_b$ has a D or an L configuration.

3. The compound of claim 2 wherein R is hydroxy; $R_1$ is methyl; $R_2$ is S; $R_3$ is absent; $R_4$ is absent; n is 1; $C_a$ has an S configuration and $C_b$ has an L configuration.

4. The compound of claim 2 wherein R is hydroxy $R_1$ is methyl; $R_2$ is O; $R_3$ is absent; $R_4$ is absent; n is 1; $C_a$ has an S configuration and $C_b$ has an L configuration.

5. The compound of claim 2 wherein R is —$NH_2$; $R_1$ is methyl; $R_2$ is S; $R_3$ is absent; $R_4$ is absent; n is 1; $C_a$ has an S configuration and $C_b$ has an L configuration.

6. The compound of claim 2 wherein R is —$NH_2$; $R_1$ is methyl; $R_2$ is O; $R_3$ is absent; $R_4$ is absent; n is 1; $C_a$ has an S configuration and $C_b$ has an L configuration.

7. The compound of claim 2 wherein R is methoxy; $R_1$ is methyl; $R_2$ is S; $R_3$ is absent; $R_4$ is absent; n is 1; $C_a$ has an S configuration and $C_b$ has an L configuration.

8. The compound of claim 2 wherein R is butoxy; $R_1$ is methyl; $R_2$ is S; $R_3$ is absent; $R_4$ is absent; n is 1; $C_a$ has an S configuration and $C_b$ has an L configuration.

9. The compound of claim 2 wherein R is butoxy; $R_1$ is methyl; $R_2$ is O; $R_3$ is absent; $R_4$ is absent; n is 1; $C_a$ has an S configuration and $C_b$ has an L configuration.

10. A compound of claim 1 which is N-[2-methyl-3-(S-pyrrolidinothioxomethyl) thiopropanoyl] L-proline.

11. A compound of claim 1 which is the methyl ester of N-[2-methyl-3-(S-pyrrolidinothioxomethyl) thiopropanoyl] L-proline.

12. A compound of claim 1 which is the t-butyl ester of N-[2-methyl-3-(S-pyrrolidinothioxomethyl) thiopropanoyl] L-proline.

13. A compound of claim 1 which is the methyl ester of N-[2-methyl-3-(S-pyrrolidinocarbonyl) thiopropanoyl] L-proline.

* * * * *